US005549474A

United States Patent [19]
Cohen

[11] Patent Number: 5,549,474
[45] Date of Patent: Aug. 27, 1996

[54] CLAMPING DEVICE PARTICULARLY USEFUL FOR DENTAL HANDPIECES

[76] Inventor: Yechiel Cohen, 4 Rotem St., Carmiel 20100, Israel

[21] Appl. No.: 315,859

[22] Filed: Sep. 30, 1994

[30] Foreign Application Priority Data

Oct. 6, 1993 [IL] Israel .......................... 107202

[51] Int. Cl.$^6$ .................................................. A61C 1/14
[52] U.S. Cl. .................................... 433/129; 279/43.2
[58] Field of Search ............................ 433/127, 129, 433/132; 279/2.04, 43.2, 46.1, 46.3, 51

[56] References Cited

U.S. PATENT DOCUMENTS

| | | |
|---|---|---|
| Re. 10, 115 | 5/1882 | Phillips . |
| 255,020 | 3/1882 | Rehfuss .......................... 433/129 |
| 1,701,172 | 8/1927 | Brown . |
| 3,035,845 | 5/1962 | Benjamin ........................ 279/51 |
| 3,074,167 | 1/1963 | Turchi et al. ..................... 32/27 |
| 3,175,293 | 3/1965 | Borden ............................ 32/27 |
| 3,252,719 | 7/1959 | Borden ............................ 285/137 |
| 3,314,153 | 4/1967 | Maurer ............................ 32/37 |
| 3,488,850 | 1/1970 | Lieb et al. ....................... 32/26 |
| 3,798,776 | 3/1974 | Lentine et al. ................... 32/26 |
| 3,869,796 | 3/1975 | Thorburn ......................... 32/26 |
| 3,888,008 | 6/1975 | Lake et al. ...................... 32/27 |
| 3,947,966 | 4/1976 | Leib et al. ...................... 32/27 |
| 3,955,284 | 5/1976 | Balson ............................ 32/27 |
| 4,114,276 | 9/1978 | Malata et al. ................... 32/26 |
| 4,279,597 | 7/1981 | Grimm ........................... 433/129 |
| 4,406,470 | 9/1983 | Kataoka et al. ................. 279/156 |
| 4,484,892 | 11/1984 | Pernot et al. ................... 433/118 |
| 4,536,157 | 8/1985 | Maizenberg ..................... 433/129 |
| 4,575,338 | 3/1986 | Maizenberg ..................... 433/126 |
| 4,595,363 | 7/1986 | Nakanishi ....................... 433/129 |
| 4,661,060 | 4/1987 | Strohmaier ...................... 433/82 |
| 4,781,589 | 11/1988 | Bareth ............................ 433/127 |
| 4,874,314 | 10/1989 | Fleer et al. ..................... 433/129 |
| 5,022,857 | 6/1991 | Matsutani et al. ................ 433/85 |
| 5,040,980 | 8/1991 | Heil .............................. 433/127 |
| 5,074,789 | 12/1991 | Shibata .......................... 433/129 |
| 5,090,906 | 2/1992 | Pernot ........................... 433/127 |
| 5,252,067 | 10/1993 | Kakimoto ....................... 433/129 |
| 5,254,004 | 10/1993 | Feldman et al. ................. 433/129 |

FOREIGN PATENT DOCUMENTS 567170  1/1945  United Kingdom ............... 279/43.2

*Primary Examiner*—Cary E. O'Connor
*Attorney, Agent, or Firm*—Ladas & Parry

[57] ABSTRACT

A clamping device for clamping a rodlike member to a housing, particularly a dental tool to a handpiece, includes a tapered sleeve and a tapered collet received within the tapered sleeve, both having open ends for receiving the rodlike member. The inner diameter of the sleeve and outer diameter of the collet decrease from their open ends to their opposite ends. The tapered collet is formed with an axial slit starting from its open end and extending along a part of its length towards its closed end, permitting the collet to contract in diameter in order to firmly clamp the rodlike member. A depressable button is engageable with the closed end of the tapered collet to move the collet outwardly of the tapered sleeve, thereby to expand the tapered collet and to permit removal or insertion of the rodlike member.

20 Claims, 2 Drawing Sheets

5,549,474

CLAMPING DEVICE PARTICULARLY USEFUL FOR DENTAL HANDPIECES

FIELD AND BACKGROUND OF THE INVENTION

The present invention relates to clamping devices for clamping a rodlike member to a housing. The invention is particularly useful in dental handpieces for clamping the shaft of a dental tool, such as a bur or drill, to the handpiece, and the invention is therefore described below with respect to this application.

One form of dental handpiece to which the invention is especially suitable is an air turbine handpiece for driving a dental tool, such as a bur or drill, at extemely high speeds, e.g. of the order of 400,000 rpm. In the existing air turbine handpieces, the clamping devices for clamping the dental tool shaft are generally of relatively bulky construction which increases the size and weight of the handpiece, and/or requires relatively awkward manipulations in order to remove and insert the dental tool into the handpiece.

OBJECTS AND BRIEF SUMMARY OF THE INVENTION

An object of the present invention is to provide a clamping device for clamping a rodlike member to a housing, which clamping may be embodied in a relatively simple, lightweight construction that can be conveniently manipulated in order to remove and insert the rodlike member. A more particular object of the present invention is to provide a dental handpiece including a clamping device having the above advantages for clamping a dental tool thereto.

According to one aspect of the present invention, there is provided a clamping device for clamping a rodlike member to a housing, comprising a tapered sleeve carried by the housing and having an inner diameter which decreases from an open end thereof to its opposite end; a tapered collet received within the open end of the tapered sleeve; the tapered collet having an open end for receiving the rodlike member, and an outer diameter which decreases from its open end to its opposite end; the tapered collet being formed with an axial slit starting from its open end and extending along at least a part of its length, permitting the part to contract in diameter in order to firmly clamp the rodlike member when received in the tapered collet and the tapered collet is received within the tapered sleeve; a depressable button carried by the housing and having an inner surface engageable with the opposite end of the tapered collet, and an outer surface engageable by a user to depress the button; and a spring normally urging said button outwardly of the housing but being depressable to move the tapered collet outwardly of the tapered sleeve, thereby to expand the part of the tapered collet to permit removal of the rodlike member from the tapered collet, or insertion of the rodlike member into the tapered collet. When the rodlike member has thus been inserted into the tapered collet, it is firmly clamped by manually pressing it and the tapered collet into the tapered sleeve.

According to further features in the described preferred embodiment, the tapered collet is formed with a plurality of the axial slits equally spaced around the circumference of the tapered collet.

In the described preferred embodiment, the plurality of axial slits terminate short of the opposite end of the tapered collet; also, the opposite end of the tapered collet is closed by an end wall formed with an enlarged head engageable by the inner surface of the depressable button.

According to another aspect of the present invention, there is provided a dental handpiece including a housing having a clamping device constructed as described above for clamping thereto a shaft of a dental tool.

As will be more particularly apparent from the description below, such a clamping device, and particularly dental handpiece, can be constructed in the form of a simple, lightweight structure which is less tiresome for the operator to hold and which can be manipulated in a convenient manner for attaching thereto and removing therefrom various rodlike members, e.g. various dental tools to a dental handpiece.

Further features and advantages of the invention will be apparent from the description below.

BRIEF DESCRIPTION OF THE DRAWINGS

The invention is herein described, by way of example only, with reference to the accompanying drawings wherein.

DESCRIPTION OF A PREFERRED EMBODIMENT

Figure 1:
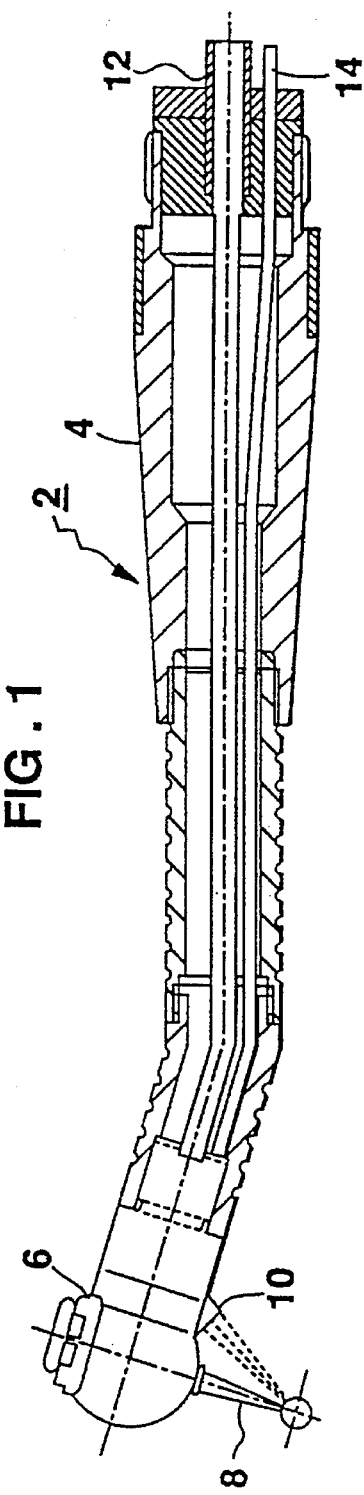
FIG. 1 is a longitudinal section view illustrating one form of dental handpiece constructed in accordance with the present invention.

With reference first to FIG. 1, there is illustrated a dental handpiece including a housing, generally designated 2, having a hand-gripping section 4 at one end, and a tool-holding section 6 at the opposite end for holding a dental tool 8, such as a bur or drill section 6 of housing 2 is further formed with a water spray nozzle 10 for discharging a water spray onto the site being worked by the dental tool 8. The dental handpiece illustrated in FIG. 1 is an air turbine handpiece in which compressed air is supplied, via a conduit 12 at the back end of the handpiece, to an air turbine within housing section 6 to rotate the dental tool 8 at a very high speed, e.g. in the order of 400,000 rpm. The rear end of the dental handpiece includes a further conduit 14 for introducing the water discharged in the form of a spray via nozzle 10 onto the working site of the dental tool.

Such dental handpieces are well known, and therefore further details of its construction are not set forth herein. The remainder of the description will, therefore, be directed primarily to the construction of the housing section 6, and particularly to the clamping device within this housing section for clamping and removing the dental tool 8, as more particularly illustrated in FIGS. 2 and 3.

Figure 2:
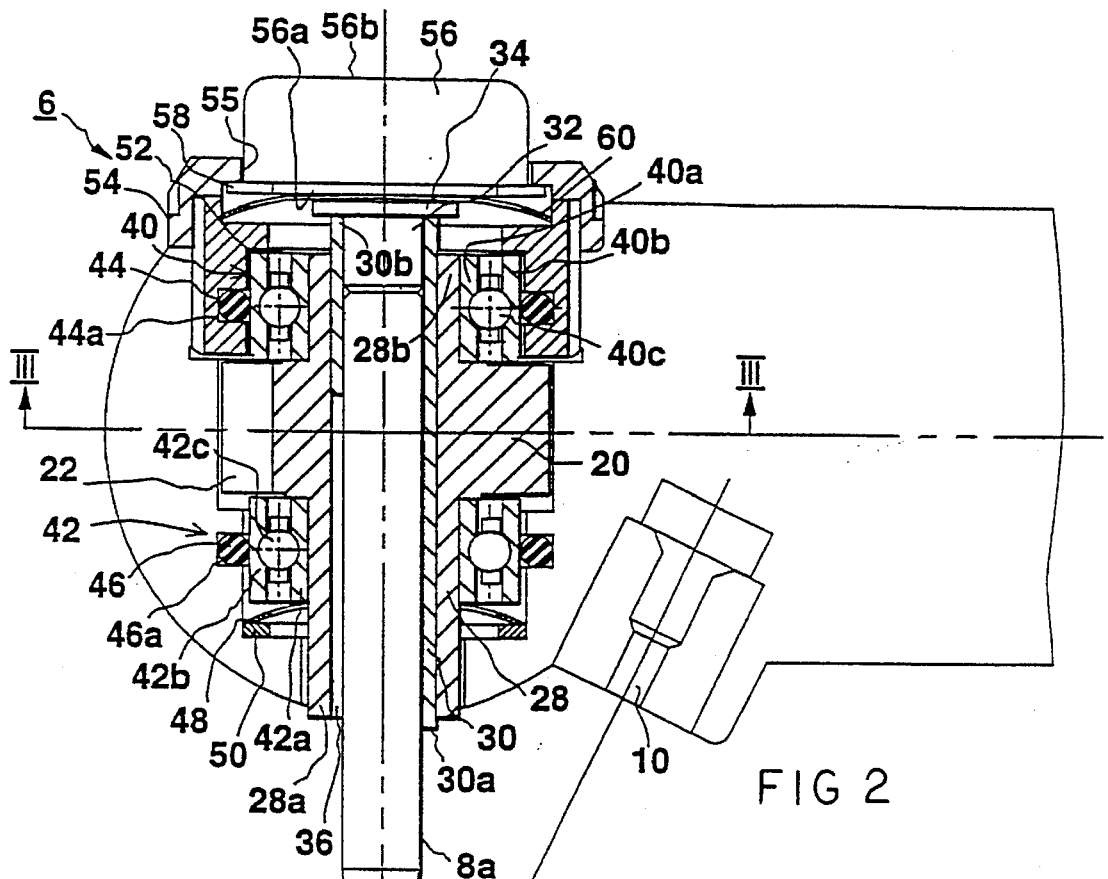
FIG. 2 is an enlarged sectional view illustrating the clamping device construction at the end of a handpiece for clamping shafts of various dental tools FIG. 2a being an enlarged fragmentary view of FIG. 2.

FIG. 2 shows, for purposes of example, the dental tool 8 as being of the bur type, including a shaft 8a of uniform diameter at one end, a bur 8b of spherical (or disc) shape at the opposite end, and a tapered juncture 8c between the shaft 8a and the bur 8b. It will be appreciated, however, that the dental tool 8 could be of another type, e.g., a drill carried at the end of the shaft.

Figure 3:
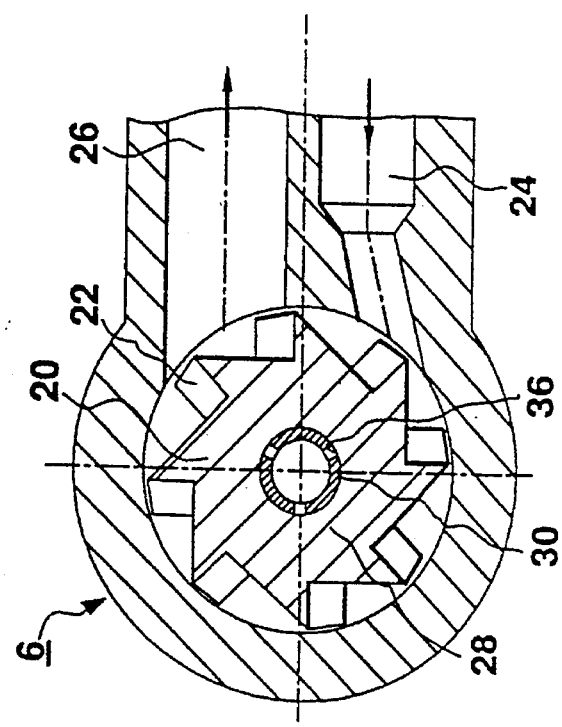
FIG. 3 is a section view along line III—III of FIG. 2.

As shown particularly in FIG. 3, housing section 6 includes an air turbine 20 formed with a plurality of blades 22 impinged by compressed air flowing from its inlet conduit 24 to its outlet conduit 26 in order to rotate the air turbine at a very high speed. Air turbine 20 is integrally formed with a sleeve 28 of tapered configuration. One end of sleeve 28 is open, as shown at 28a, for receiving the shaft 8a of the dental tool 8. The inner diameter of tapered sleeve 28 decreases from its open end 28a to its opposite end 28b, which is also open.

Figure 2A:
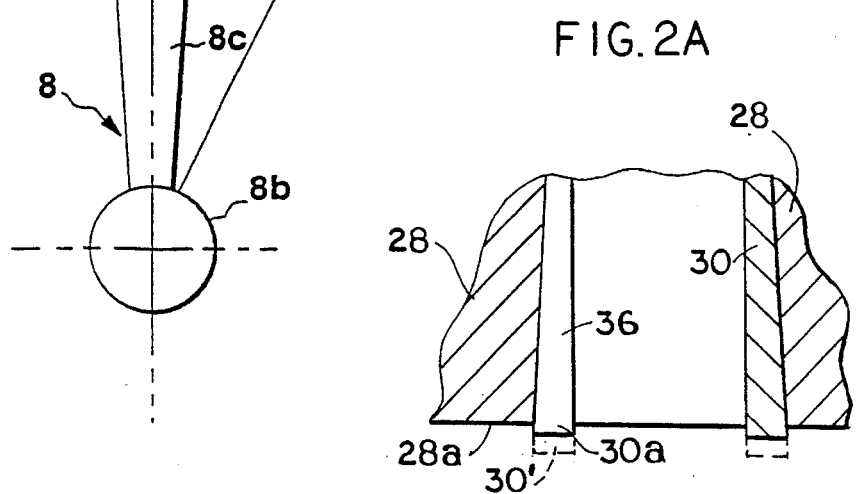

Tapered sleeve 28 which, as noted above, is integrally formed with the air turbine 20, receives a tapered collet 30. Tapered collet 30 is also formed with an open end 30a received within the open end 28a of the tapered sleeve 28 for receiving the shaft 8a of the dental tool 8. The outer diameter of tapered collet 30 decreases from its open end 30a to its opposite end 30b, as more particularly seen in FIG. 2a. Its opposite end 30b is closed by an end wall or plug 32 formed within an enlarged head 34.

Tapered collet 30 is further formed with three axial slits 36, equally-spaced around its circumference as shown in FIG. 3. Slits 36 start at its open end 30a and extend only for a part of the length of the collet towards opposite end 30b.

In the example illustrated in the drawings, slits 36 extend about two-thirds the length of the tapered collet 30. As will be described more particularly below, the slits 36 permit the respective section of the tapered collet to contract in order to firmly clamp therein the shaft 8a of the dental tool, or to expand in order to release the shaft for purposes of removing the dental tool or reinserting another dental tool in its place.

Housing section 6 further includes two ball-bearing assemblies 40, 42, at the opposite sides of the axis of housing section 6 for rotatably mounting the air turbine 20, its tapered sleeve 28, the tapered collet 30, and the dental tool 8 when clamped therein, with respect to the housing. Thus, each ball-bearing assembly 40, 42 includes: a rotary ring 40a, 42a; a static ring 40b, 42b; and a plurality of balls 40c, 42c interposed between both rings.

Housing section 6 further includes a vibration-absorbing O-ring 44, 46, for each of the ball-bearing assemblies 40, 42. Each O-ring 44, 46 is received within an annular recess 44a, 46a, formed in housing section 6 and bearing against the static ring 40b, 42b, of the respective assembly.

Housing section 6 further includes a spring 48 baring against a plastic ring 50 e.g. of "Teflon" (Reg T.M.) for preloading the static part of the bearing in order to reduce vibration during the high-speed rotation of the dental tool. A similar plastic ring 52 is provided at the opposite end of the housing section 6 cooperable with bearing assembly 40.

The latter end of housing section 6 is closed by a collar 54 treadedly attached to the housing section and formed with a central opening 55 in which a button 56 is mounted to project through the opening. Button 56 is formed with an outwardly-projecting rim 58 around its circumference engageable by the edge of collar 54 circumscribing opening 55 receiving the button. An annular spring 60 is interposed between the housing section 6 and button 56. Spring 60 is engageable within inner surface 56a of the button to urge the button outwardly, limited by the engagement of rim 58 of the button with the undersurface of collar 54. Button 56, however, is depressable inwardly of the housing section 6 against spring 60, by pressing against the outer surface 56b of the button, to bring the inner surface 56a of the button into engagement with the enlarged head 34 of the tapered collet 30, and thereby to move the tapered collet outwardly of the tapered sleeve 28.

It will thus be seen that in order to remove the dental tool 8 from the housing section 6, the outer surface 56b of the button is manually engaged to depress button 56 against the action of spring 60. This causes the inner surface 56a of button 56 to engage the enlarged head 34 of the tapered collet 30, and to move the tapered collet outwardly of the tapered sleeve 28, as shown by broken lines 30' in FIG. 2a. When this occurs, the slits 36 formed in the outer two-thirds section of the tapered collet 30 permit that section of the tapered collet, moving outwardly of the tapered sleeve 28 to expand and thereby to release the shaft 8a of the dental tool. The dental tool may then be manually grasped and removed from the tapered collet 30.

When it is desired to insert another dental tool 8, button 56 is again depressed to move the tapered collet 30 outwardly of the tapered sleeve 28, thereby providing a relatively large diameter for the tapered collet to receive the shaft 8a of the dental tool 8. While the button is still depressed, the dental tool is pushed inwardly into the tapered collet 30 until the end of the dental tool shaft 8a limits against the end wall 32 of the tapered collet. At that time, button 56 is released, whereupon spring 60 moves the button 56 slightly outwardly of the housing. The user then manually pushes the dental tool shaft 8a further inwardly into the housing. This also moves the tapered collet 30 and its projected end 30' (FIG. 2a) further into the housing, until the enlarged head 34 of the tapered collet limits against the inner surface 56a of the button 56, at which time the dental tool 8 is firmly clamped in housing section 6 by the wedging action between the tapered collet 30 and the tapered sleeve 28.

In a preferred construction, the tapered collet 30 and the tapered sleeve 28 both may have a taper of 1:40; the housing 4, including housing section 6, the air turbine 20 including its blades 22 and its tapered sleeve 28, and the tapered collet 30, may all be made of anodized aluminium; and both the inner and outer surfaces of the tapered collet 30 and the inner surface of the tapered sleeve 28 may be plated with hard electroless nickel.

While the invention has been described with respect to one preferred embodiment, it will be appreciated that many variations, modifications and other applications of the invention may be made.

What is claimed is:

1. A clamping device for clamping a rodlike member to a housing, comprising:

a tapered sleeve carried by said housing and having an inner diameter which decreases from an open end thereof to its opposite end;

a tapered collet received within said open end of the tapered sleeve; said tapered collet having an open end for receiving the rodlike member, and an outer diameter which decreases from its open end to its opposite end; said tapered collet being formed with an axial slit starting from its open end and extending along at least a part of its length, permitting said part to contract in diameter in order to firmly clamp the rodlike member when received in the tapered collet and the tapered collet is received within the tapered sleeve;

a depressable button carried by said housing and having an inner surface engageable with said opposite end of the tapered collet, and an outer surface engageable by a user to depress the button;

and a spring normally urging said button outwardly of the housing but being depressable to move the tapered collet outwardly of the tapered sleeve, thereby to expand said part of the tapered collet to permit removal of the rodlike member from the tapered collet, or insertion of the rodlike member into the tapered collet and firm clamping of the rodlike member in the tapered collet by manually pressing the rodlike member and tapered collet into the tapered sleeve.

2. The clamping device according to claim 1, wherein said tapered collet is formed with a plurality of said axial slits equally spaced around the circumference of the tapered collet.

3. The clamping device according to claim 2, wherein said plurality of axial slits terminate short of said opposite end of the tapered collet.

4. The clamping device according to claim 1, wherein said opposite end of the tapered collet is closed by an end wall formed with an enlarged head engageable by said inner surface of the depressable button.

5. The clamping device according to claim 1, wherein said depressable button is received within an opening formed in a collar fixed to said housing, and said spring is an annular spring which urges the depressable button against the inner surface of the collar around said opening.

6. The clamping device according to claim 1, wherein said tapered sleeve is carried by a rotary drive member.

7. The clamping device according to claim 6, wherein said rotary drive member is an air turbine having a plurality of blades for rotating said tapered collet and said rodlike member when clamped therein.

8. The clamping device according to claim 7, wherein said tapered sleeve is integrally formed with said air turbine.

9. The clamping device according to claim 6, wherein said housing includes a bearing rotatably mounting said rotary drive member, tapered sleeve, tapered collet and rodlike member when clamped therein, with respect to said housing; said bearing including a static section and a rotatable section; said clamping device further including a resilient, vibration-absorbing O-ring interposed between the housing and the static section of the bearing.

10. The clamping device according to claim 9, wherein said housing includes two of said bearings on opposite sides thereof, and two of said resilient, vibration-absorbing O-rings, one for each of said bearings.

11. The clamping device according to claim 6, wherein said housing is a dental handpiece for receiving the rodlike shaft of a dental tool.

12. A dental handpiece including a housing having a clamping device for clamping thereto a shaft of a dental tool, comprising:

a tapered sleeve carried by said housing and having an inner diameter which decreases from an open end thereof to its opposite end;

a tapered collet received within said open end of the tapered sleeve; said tapered collet having an open end for receiving the dental tool shaft, and an outer diameter which decreases from its open end to its opposite end; said tapered collet being formed with an axial slit starting from its open end and extending along at least a part of its length, permitting said part to contract in diameter in order to firmly clamp the dental tool shaft when received in the tapered collet and the tapered collet is received within the tapered sleeve;

a depressable button carried by said housing and having an inner surface engageable with said opposite end of the tapered collet, and an outer surface engageable by a user to depress the button;

and a spring normally urging said button outwardly of the housing but being depressable to move the tapered collet outwardly of the tapered sleeve, thereby to expand said part of the tapered collet to permit removal of the dental tool shaft from the tapered collet, or insertion of the dental tool shaft into the tapered collet and firm clamping of the rodlike member in the tapered collet by manually pressing the rodlike member and tapered collet into the tapered sleeve.

13. The dental handpiece according to claim 12, wherein said rotary drive member is an air turbine having a plurality of blades for rotating said tapered collet and said dental tool shaft when clamped therein.

14. The dental handpiece according to claim 13, wherein said tapered sleeve is integrally formed with said air turbine.

15. The dental handpiece according to claim 12, wherein said housing includes a bearing rotatably mounting said rotary drive member, tapered sleeve, tapered collet and dental tool shaft where clamped therein, with respect to said housing; said bearing including a static section, and a rotatable section; said clamping device further including a resilient, vibration-absorbing O-ring interposed between the housing and the static section of the bearing.

16. The dental handpiece according to claim 15, wherein said housing includes two of said bearings on opposite sides thereof, and two of said resilient, vibration-absorbing O-rings, one for each of said bearings.

17. The dental handpiece according to claim 12, wherein said tapered collet is formed with a plurality of said axial slits equally spaced around the circumference of the tapered collet.

18. The dental handpiece according to claim 17, wherein said plurality of axial slits terminate short of said opposite end of the tapered collet.

19. The dental handpiece according to claim 12, wherein said opposite end of the tapered collet is closed by an end wall formed with an enlarged head engageable by said inner surface of the depressable button.

20. The dental handpiece according to claim 12, wherein said depressable button is received within an opening formed in a collar fixed to said housing, and said spring is an annular spring which urges the depressable button against the inner surface of the collar around said opening.

* * * * *